US012642979B2

(12) United States Patent
Wu et al.

(10) Patent No.: US 12,642,979 B2
(45) Date of Patent: Jun. 2, 2026

(54) RECYCLING DOCKING ASSEMBLY, CONVEYING APPARATUS, LEADLESS PACEMAKER, AND PACEMAKER SYSTEM

(71) Applicant: MICROPORT SOARING CRM (SHANGHAI) CO., LTD., Shanghai (CN)

(72) Inventors: Nan Wu, Shanghai (CN); Zhijun Cheng, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 65 days.

(21) Appl. No.: 18/714,386

(22) PCT Filed: Oct. 21, 2022

(86) PCT No.: PCT/CN2022/126549
§ 371 (c)(1),
(2) Date: May 29, 2024

(87) PCT Pub. No.: WO2023/098331
PCT Pub. Date: Jun. 8, 2023

(65) Prior Publication Data
US 2025/0339698 A1 Nov. 6, 2025

(30) Foreign Application Priority Data
Nov. 30, 2021 (CN) .......................... 202111446980.4

(51) Int. Cl.
*A61N 1/375* (2006.01)
*A61B 17/00* (2006.01)

(52) U.S. Cl.
CPC .... *A61N 1/37512* (2017.08); *A61B 17/00234* (2013.01); *A61N 1/3756* (2013.01); *A61B 2017/00358* (2013.01)

(58) Field of Classification Search
CPC .............. A61N 1/3756; A61N 1/37205; A61N 1/0573; A61N 1/37518; A61N 1/3956;
(Continued)

(56) References Cited

U.S. PATENT DOCUMENTS

2015/0051611 A1* 2/2015 Schmidt .............. A61N 1/3756
606/129
2017/0281952 A1 10/2017 Shuros et al.
(Continued)

FOREIGN PATENT DOCUMENTS

CN 103402578 B 3/2016
CN 109922745 A 6/2019
(Continued)

*Primary Examiner* — Mohamed G Gabr
(74) *Attorney, Agent, or Firm* — MUNCY, GEISSLER, OLDS & LOWE, P.C.

(57) ABSTRACT

A retrieval docking component includes a base and a limiting part. A distal end of the base along an axial direction is configured for connection with a body of an implantable medical device, and a proximal end of the base along an axial direction is connected to the limiting part. A radial outer dimension of the limiting part is greater than a radial outer dimension of the proximal end of the base. The limiting part includes at least two accommodation grooves along its circumference, which are open outwardly in radial direction of the limiting part and configured for capture a snare of a delivery device. The structure of the retrieval docking component provides adequate and reasonable accommodation space to the retrieval snare in a limited space, enabling the delivery device conveniently and reliably form a connection with the retrieval docking component, increasing success rate of retrieval and docking.

19 Claims, 7 Drawing Sheets

(58) Field of Classification Search
CPC ........ A61N 1/39622; A61N 2001/0578; A61N 2001/058; A61N 2001/0585; A61B 2017/00358; A61B 2017/22035; A61B 2017/00243; A61B 17/221; A61B 17/32056; A61B 17/3468
See application file for complete search history.

(56) References Cited

U.S. PATENT DOCUMENTS

| | | | |
|---|---|---|---|
| 2019/0275340 A1* | 9/2019 | Eby ........................ | A61N 1/372 |
| 2021/0282808 A1 | 9/2021 | Goodman et al. | |

FOREIGN PATENT DOCUMENTS

| | | |
|---|---|---|
| CN | 110944714 A | 3/2020 |
| CN | 216725530 U | 6/2022 |

* cited by examiner

220

230                                    230

230                230

220

230                                    230

230                                    230

RECYCLING DOCKING ASSEMBLY, CONVEYING APPARATUS, LEADLESS PACEMAKER, AND PACEMAKER SYSTEM

TECHNICAL FIELD

The present application relates to the field of medical devices and, in particular, to a retrieval docking component, a delivery device, a leadless pacemaker and a pacemaker system.

BACKGROUND

Leadless pacemakers nowadays are typically composed of, among others, a proximal end of a leadless pacemaker, a packaging housing, a ring electrode, a battery, electrical components, a distal end of a leadless pacemaker, and a head electrode, and are principally implanted into a patient's ventricle to sense pacing pulses. The distal end of a leadless pacemaker includes a fixation element, which is configured to attach to the inner wall of the ventricle, and the proximal end of a leadless pacemaker includes a retrieval docking structure, which is configured to partial or entire retrieve the pacemaker from the patient's body, if desired. However, since the leadless pacemaker is desired to have a small overall size (usually not greater than 1.2 cm³), the retrieval docking structure in the proximal end of the leadless pacemaker has a relative small size. This, however, increases the difficulty in aligning and docking the retrieval docking structure with a retrieval system. In particular, when the distal end employs an active helical fixation method, after docking, the retrieval docking structure at the proximal end is also required to function for torque transmission and to be easily centered to facilitate its entry into a retrieval cup of a delivery device. Therefore, this structure is subject to stringent requirements. The success rate of capturing and retrieving a leadless pacemaker using the delivery device largely depends on the probability of successful docking between the retrieval docking structure and the delivery device, as well as the operator's experience. Therefore, such leadless pacemakers are associated with difficult docking and fail to provide a high success rate in retrieval.

SUMMARY OF THE INVENTION

It is an object of the present application to provide a retrieval docking component, a delivery device, a leadless pacemaker and a pacemaker system, to solve the problem of the capture and retrieval of conventional leadless pacemakers, which rely on operator's experience and has low success rate.

To this end, in a first aspect of the present application, there is provided a retrieval docking component for an implantable medical device, which comprises a base and a limiting part, wherein a distal end of the base along an axial direction is to be connected to a body of the implantable medical device, wherein a proximal end of the base along the axial direction is connected to the limiting part, and wherein the limiting part has a radial outer dimension that is greater than a radial outer dimension of the proximal end of the base, wherein the limiting part comprises at least two accommodation grooves along its circumference, and wherein the accommodation groove is open outwardly along a radial direction of the base and is configured to capture a snare of a delivery device.

Optionally, the radial outer dimension of the base gradually decreases from the distal end to the proximal end.

Optionally, the accommodation groove extends along an axis of the base and extends through the limiting part.

Optionally, in the retrieval docking component, the accommodation groove comprises, along its direction of extension, an imaginary centerline plane and two groove wall surfaces on opposite sides of the imaginary centerline plane, wherein at least one groove wall surface of at least one accommodation groove comprises a first guide surface, and the first guide surface is gradually away from the imaginary centerline plane along a direction towards an exterior of the limiting part, thereby forming a flared opening.

Optionally, in the retrieval docking component, the accommodation groove comprises, along its direction of extension, an imaginary centerline plane and two groove wall surfaces on opposite sides of the imaginary centerline plane, wherein the limiting part comprises a second guide surface, and the second guide surface is joined to at least one groove wall surface and is gradually away from the imaginary centerline plane along a direction towards the distal end.

Optionally, in the retrieval docking component, the accommodation groove comprises, along its direction of extension, an imaginary centerline plane and a groove bottom surface intersecting the imaginary centerline plane, wherein the groove bottom surface of at least one accommodation groove comprises a third guide surface, and the groove bottom surface extends to the proximal end and gradually approaches the axis of the base as extending.

Optionally, in the retrieval docking component, the radial outer dimension of the limiting part gradually decreases from distal end to proximal end.

Optionally, in the retrieval docking component, the limiting part comprises a stop surface that is oriented towards the distal end, wherein the stop surface forms an angle not greater than 90° with a direction pointing to the distal end along an axis of the base.

Optionally, in the retrieval docking component, the limiting part comprises a docking structure oriented towards the proximal end, wherein the docking structure comprises a center coincident with an axis of the base and is configured to mate with a sheath of the delivery device.

Optionally, in the retrieval docking component, the limiting part comprises four accommodation grooves uniformly distributed along its circumference.

Optionally, the retrieval docking component further comprises a capture wing, wherein the capture wing comprises a first end connected to the limiting part and a second end, and the second end is a free end, the capture wing comprising, when not stressed, an uncollapsed configuration in which the capture wing is gradually outwardly as extending towards the distal end of the base, wherein a distance from the free ends to an axis of the base is greater than a maximum distance between an outer periphery of the limiting part and the axis of the base.

Optionally, in the retrieval docking component, the capture wing is transitioned under the action of an external confining structure into a collapsed configuration;

wherein when the capture wing is in the collapsed configuration, the free end extends towards the distal end and wherein a distance from the free end to the axis of the base is not greater than the maximum distance between the outer periphery of the limiting part and the axis of the base.

Optionally, in the retrieval docking component, the capture wings are elastic sheets and achieve a transition between the uncollapsed and collapsed configurations by elastic deformation.

Optionally, the retrieval docking component comprises two capture wings, wherein the limiting part comprises two accommodation grooves along its circumference, and the capture wings and the accommodation grooves are alternately arranged uniformly along the circumference of the limiting part.

To the above end, in a second aspect of the present application, there is provided a delivery device configured to be connected to the retrieval docking component as defined above. The delivery device comprises a snare and sheath, wherein the snare is movably disposed along an axis of the sheath, wherein the snare is configured to loop around the exterior of an implantable medical device, wherein during the snare gradually moves towards the proximal end with respect to the sheath, the snare moves to the base of the retrieval docking component, then slides along the retrieval docking component until coming into abutment against the limiting part, and is captured in the accommodation groove, wherein the sheath comprises a distal end configured to be aligned with a proximal end of the limiting part, and to abut and engage the proximal end of the limiting part under an action of the snare being retracted to the proximal end.

Optionally, in the delivery device, the snare comprises a U-shaped section located at the distal end and extensions joined to the U-shaped section at open ends thereof, wherein when the snare is in an initial configuration where it is not stressed, an extending direction of the U-shaped section forms an angle with an extending direction of the extension.

Optionally, the delivery device further comprises a retrieval cup, the retrieval cup is movably disposed along the axis of the sheath, wherein the retrieval cup comprises a distal end that is open, wherein the retrieval cup is configured to sheathe the retrieval docking component and a body of the implantable medical device from a proximal end to a distal end of the retrieval docking component.

To the above end, in a third aspect of the present application, there is provided a leadless pacemaker, which comprises a leadless pacemaker body and the retrieval docking component as defined above, wherein the base of the retrieval docking component is connected to a proximal end of the leadless pacemaker body.

To the above end, in a fourth aspect of the present application, there is provided a leadless pacemaker system, which comprises the delivery device as defined above and the leadless pacemaker as defined above.

In summary, the present application provides a retrieval docking component, a delivery device, a leadless pacemaker and a pacemaker system. The retrieval docking component includes a base and a limiting part. A distal end of the base along the axial direction is configured for connection with a body of an implantable medical device, and a proximal end of the base along the axial direction is connected to the limiting part. A radial outer dimension of the limiting part is greater than a radial outer dimension of the proximal end of the base. The limiting part comprises at least two accommodation grooves along its circumference, which are open outwardly along radial direction of the limiting part and configured to capture a snare of a delivery device.

With this arrangement, the structure of the retrieval docking component is simple and provides adequate and reasonable accommodation space to the retrieval snare in a limited space. After the snare of the delivery device loops the implantable medical device, and moving and retracted towards the proximal end, it can slide along the base to abut and engage with the limiting part, and capture in the accommodation grooves. In this way, enabling the delivery device conveniently and reliably form a connection with the retrieval docking component, increasing success rate of retrieval and docking between the retrieval docking component and the delivery device and reducing the docking difficulty. Further, when the snare is captured in the accommodation grooves, it can also adapt for torque transmission and easy aligning and docking between the delivery device and the retrieval docking component with respect to each other, increasing convenience in retrieval of the implantable medical device.

BRIEF DESCRIPTION OF THE DRAWINGS

Those of ordinary skill in the art would appreciate that the following drawings are presented merely to enable a better understanding of the present application rather than to limit the scope thereof in any sense, in which.

Figure 1:
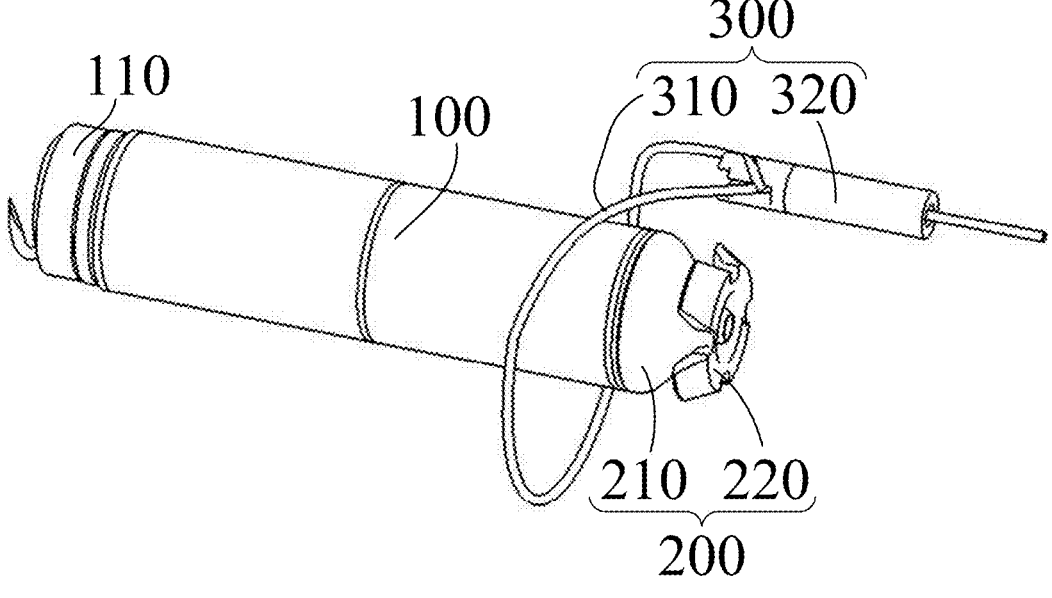
FIG. 1 schematically illustrates a leadless pacemaker and a delivery device according to an embodiment of the present application, which have not been connected to each other yet.

In these figures, 100, leadless pacemaker body; 110, fixation element; 200, a retrieval docking component; 210, a base; 220, a limiting part; 221, a second guide surface; 222, a stop surface; 223, a docking structure; 230, an accommodation groove; 231, an imaginary centerline plane; 232, a groove wall surface; 2321, a first guide surface; 233, a flared opening; 234, a groove bottom surface; 2341, a third guide surface; 240, a capture wing;

300, a delivery device; 310, a snare; 311, a U-shaped section; 312, an extension; 320, a sheath; and 330, a retrieval cup.

DETAILED DESCRIPTION

Objects, features and advantages of the present application will become more apparent upon reading the following more detailed description, which is set forth by way of particular embodiments with reference to the accompanying drawings. Note that the figures are provided in a very simplified form not necessarily drawn to exact scale for the only purpose of helping to explain the disclosed embodiments in a more convenient and clearer way. In addition, structures shown in the figures are usually a part of actual structures. In particular, as the figures tend to have distinct emphases, they are often drawn to different scales.

As used herein, the singular forms "a", "an" and "the" include plural referents. As used herein, the term "or" is generally employed in the sense of "and/or", "several" is generally employed in the sense of "at least one" and "at least two" is generally employed in the sense of "two or more". Additionally, the use of the terms "first", "second" and "third" herein is intended for illustration only and is not to be construed as denoting or implying relative importance or as implicitly indicating the numerical number of the referenced item. Accordingly, defining an item with "first", "second" or "third" is an explicit or implicit indication of the presence of one or at least two such items. The term "proximal end" generally refers to an end closer to an operator, and the term "distal end" generally refer to an end closer to a lesion in a patient (i.e., farther away from the operator). The terms "one end" and "the other end", as well as "proximal end" and "distal end", are generally used to refer to opposite ends including the opposite endpoints, rather than only to the endpoints. The terms "mounting", "coupling" and "connection" should be interpreted in a broad sense. For instance, a connection may be a permanent, detachable or integral connection, or a mechanical or electrical connection, or a direct or indirect connection with one or more intervening media, or an internal communication or interaction between two elements. As used herein, when an element is referred to as being "disposed on" another element, this is generally intended to only mean that there is a connection, coupling, engagement or transmission relationship between the two elements, which may be either direct or indirect with one or more intervening elements, and should not be interpreted as indicating or implying a particular spatial position relationship between the two elements, i.e., the element may be located inside, outside, above, under, beside, or at any other location with respect to the other element, unless the context clearly dictates otherwise. Those of ordinary skill in the art can understand the specific meanings of the above-mentioned terms herein, depending on their context.

A description is set forth with reference to the accompanying drawings.

Figure 2:
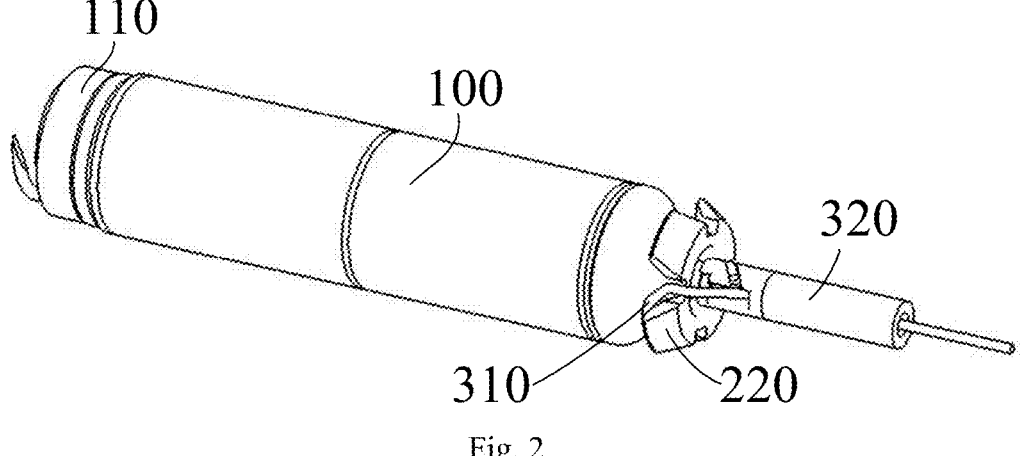
FIG. 2 schematically illustrates a leadless pacemaker and a delivery device according to an embodiment of the present application, which have been connected to each other.
Figure 3:
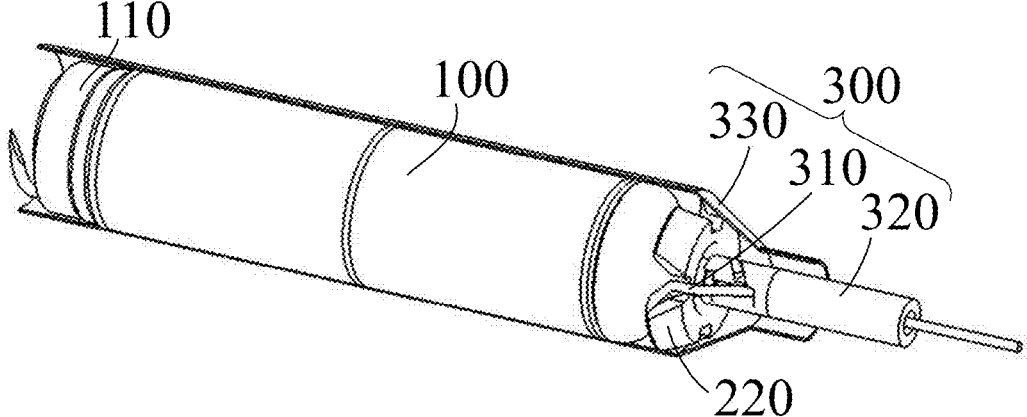
FIG. 3 schematically illustrates a leadless pacemaker according to an embodiment of the present application, which has been captured in a retrieval cup.
Figure 4:
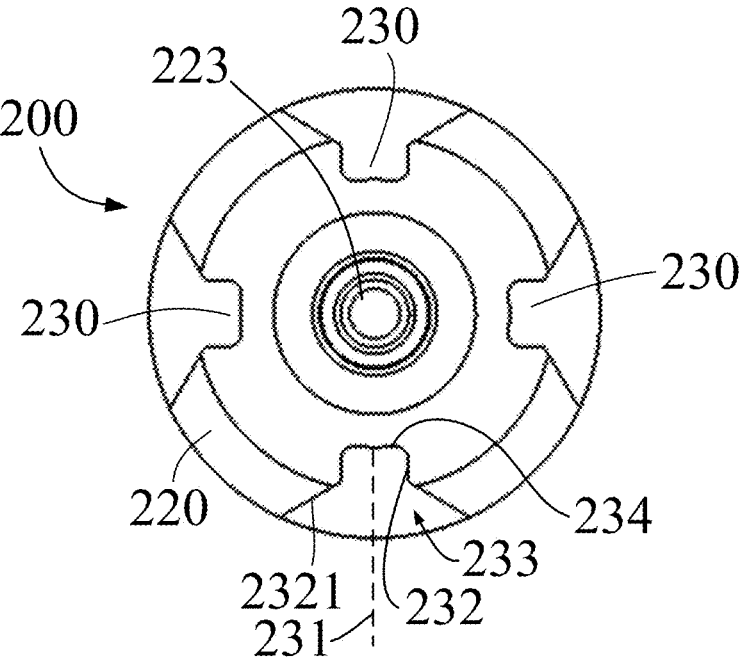
FIG. 4 shows a proximal end of a retrieval docking component according to an embodiment of the present application.
Figures 5, 6:
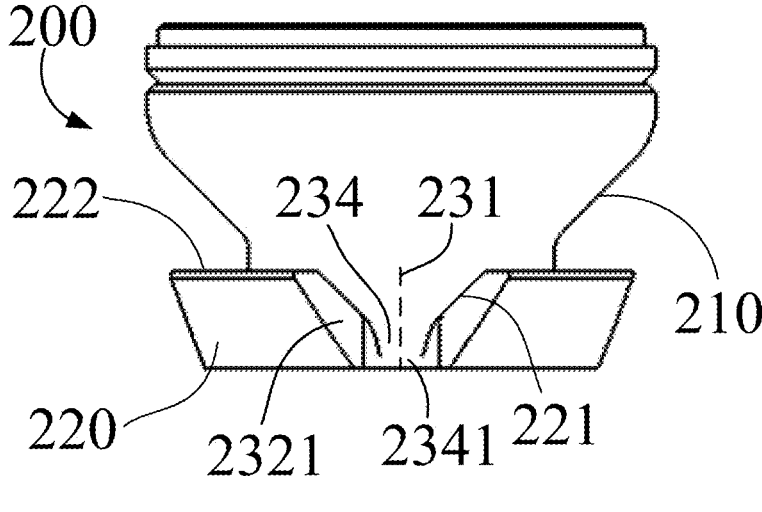
FIG. 5 is a side view of the retrieval docking component of FIG. 4.
FIG. 6 is a schematic illustration of a snare according to an embodiment of the present application.
Figures 7, 8:
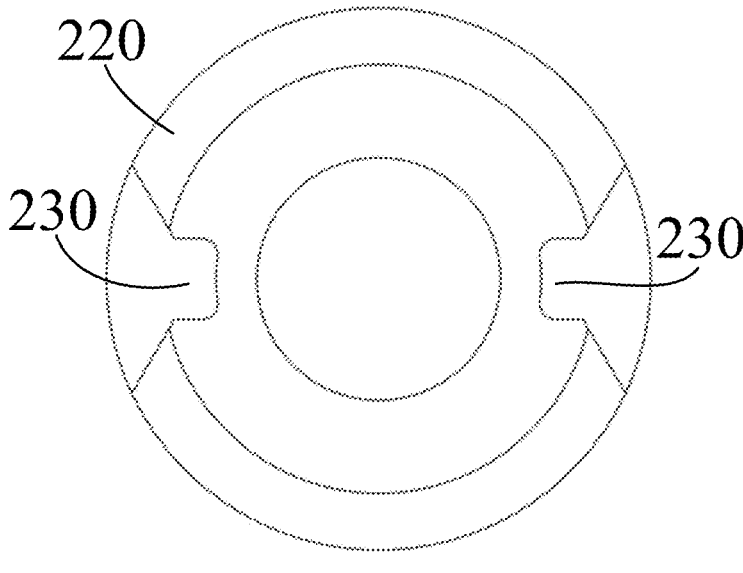
FIG. 7 shows a comparative example of a limiting part according to an embodiment of the present application.
FIG. 8 shows another comparative example of the limiting part according to an embodiment of the present application.
Figure 9:
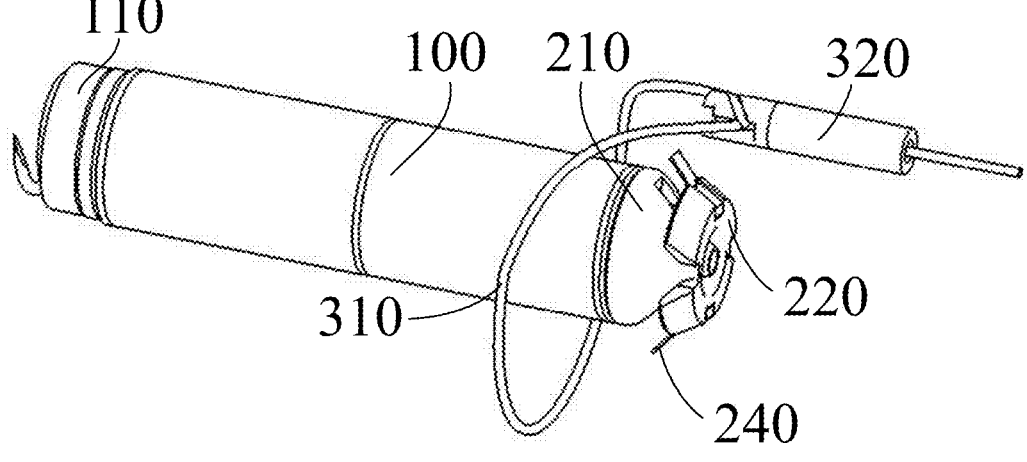
FIG. 9 schematically illustrates a leadless pacemaker and a delivery device according to another embodiment of the present application, which have not been connected to each other yet.
Figure 10:
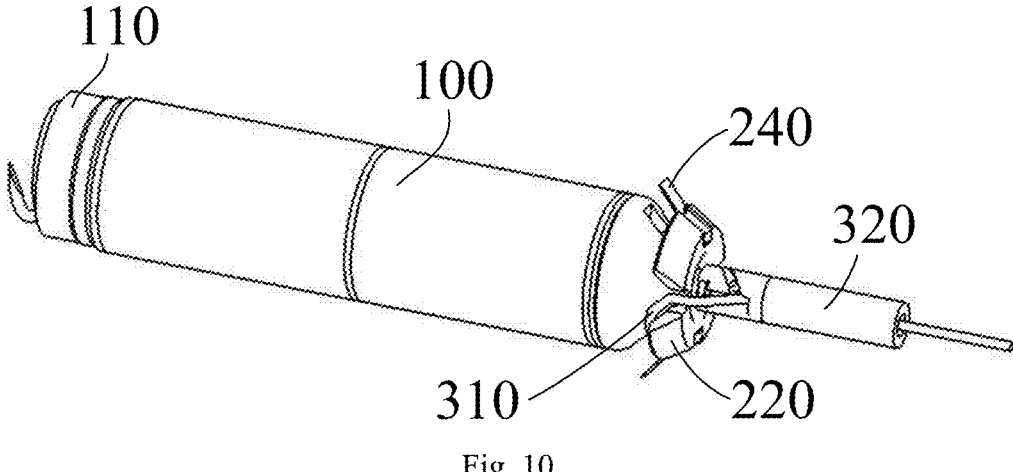
FIG. 10 schematically illustrates a leadless pacemaker and a delivery device according to another embodiment of the present application, which have been connected to each other.
Figure 11:
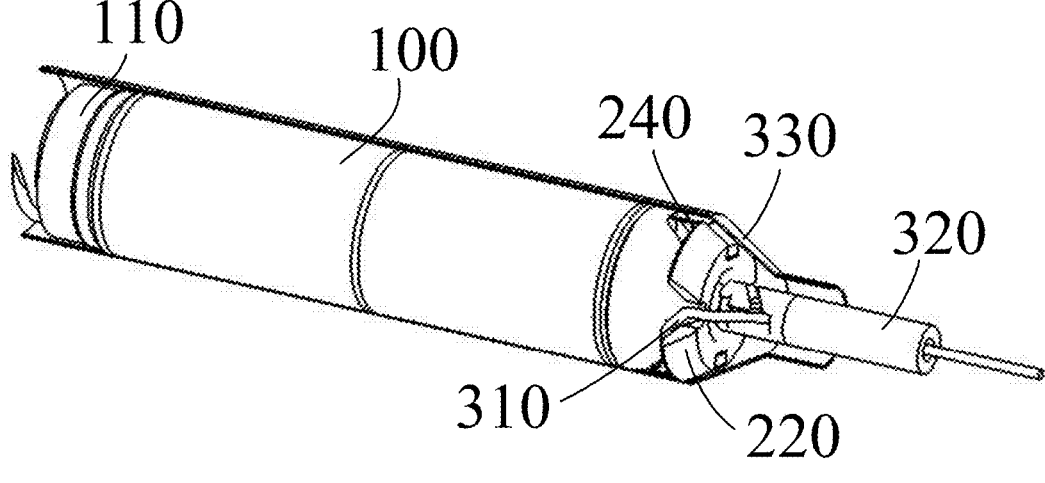
FIG. 11 schematically illustrates a leadless pacemaker according to another embodiment of the present application, which has been captured in a retrieval cup.
Figure 12:
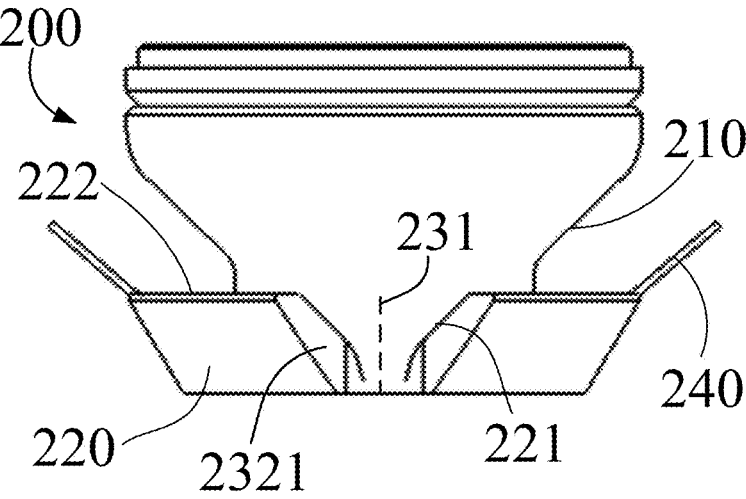
FIG. 12 shows a proximal end of a retrieval docking component according to another embodiment of the present application, in which capture wings are in an uncollapsed configuration.
Figure 13:
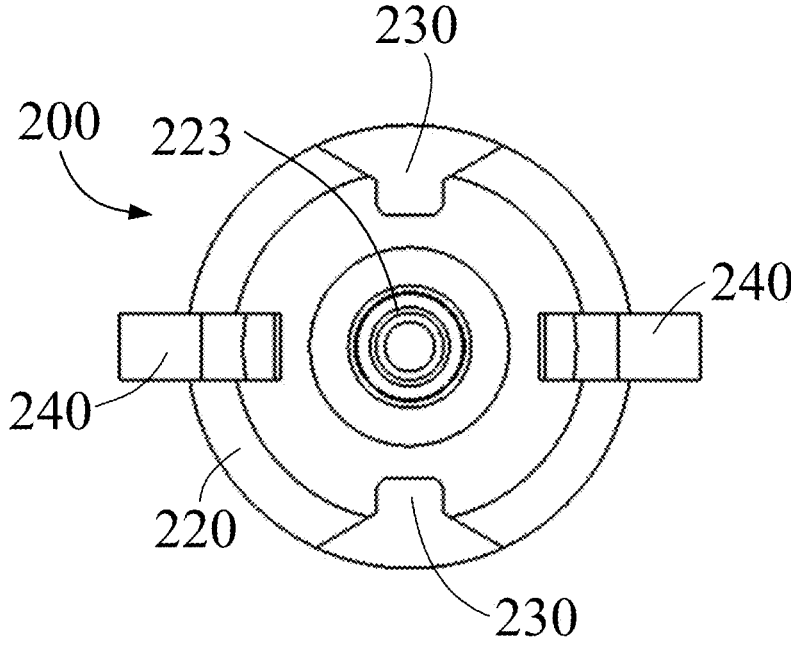
FIG. 13 is a side view of the retrieval docking component of FIG. 12.
Figure 14:
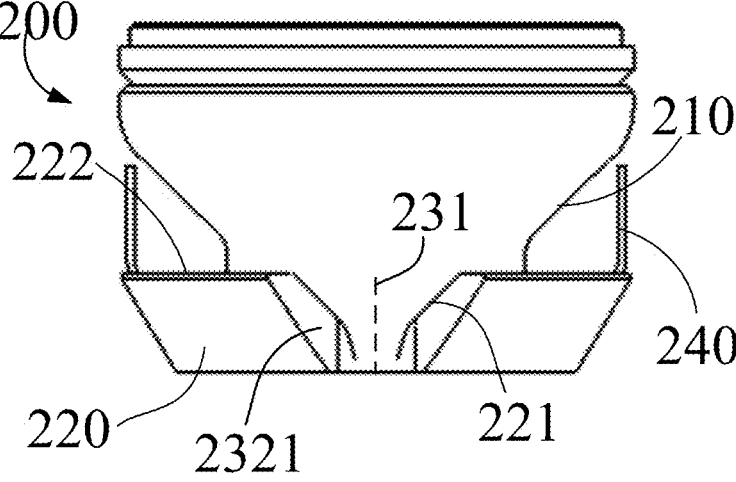
FIG. 14 shows a proximal end of a retrieval docking component according to yet another embodiment of the present application, in which capture wings are in a collapsed configuration.

Reference is made below to FIGS. 1 to 14. FIG. 1 schematically illustrates a leadless pacemaker and a delivery device according to an embodiment of the present application, which have not been connected to each other yet. FIG. 2 schematically illustrates a leadless pacemaker and a delivery device according to an embodiment of the present application, which have been connected to each other. FIG. 3 schematically illustrates a leadless pacemaker according to an embodiment of the present application, which has been captured in a retrieval cup. FIG. 4 shows a proximal end of a retrieval docking component according to an embodiment of the present application. FIG. 5 is a side view of the retrieval docking component of FIG. 4. FIG. 6 is a schematic illustration of a snare according to an embodiment of the present application. FIG. 7 shows a comparative example of a limiting part according to an embodiment of the present application. FIG. 8 shows another comparative example of the limiting part according to an embodiment of the present application. FIG. 9 schematically illustrates a leadless pacemaker and a delivery device according to another embodiment of the present application, which have not been connected to each other yet. FIG. 10 schematically illustrates a leadless pacemaker and a delivery device according to another embodiment of the present application, which have been connected to each other. FIG. 11 schematically illustrates a leadless pacemaker according to another embodiment of the present application, which has been captured in a retrieval cup. FIG. 12 shows a proximal end of a retrieval docking component according to another embodiment of the present application, in which capture wings are in an uncollapsed configuration. FIG. 13 is a side view of the retrieval docking component of FIG. 12. FIG. 14 shows a proximal end of a retrieval docking component according to yet another embodiment of the present application, in which capture wings are in a collapsed configuration.

In interventional treatment, it is often necessary to use a delivery device to deliver an implantable medical device to a predetermined site through a natural lumen in a patient's body and fix it at the predetermined site. In some application scenarios, after the implantation, it is also necessary to use a delivery device to remove the implantable medical device from the predetermined site to facilitate adjustment of the implant site, or replacement and maintenance of the implantable medical device. Here, according to the present application, non-limiting examples of the implantable medical device may include leadless pacemakers.

A description is set forth below with reference to FIGS. 1 to 3 in the context of the implantable medical device being a leadless pacemaker, as an example. It should be understood that the leadless pacemaker is merely a non-limiting example of the implantable medical device, and any person of skill in the art may configure a retrieval docking component 200 on other implantable medical devices in accordance with embodiments of the present application, and retrieve and dock the implantable medical device with a corresponding delivery device 300.

The leadless pacemaker includes a leadless pacemaker body 100 and a retrieval docking component 200, and a distal end of the retrieval docking component 200 (the left end in FIG. 1) is connected to a proximal end of the pacemaker body 100 (the right end in FIG. 1). Here, the connection of the retrieval docking component 200 and the pacemaker body 100 may be fixed, e.g., welded, adhesive or integral, or detachable, e.g., snap or threaded. In the example of FIGS. 1 to 3, the leadless pacemaker body 100 is generally cylindrical, and its distal end (the left end in FIG. 1) includes a fixation element 110, which is configured to pierce and anchor to the heart at a predetermined site, for example, barb fixation after screwing, piercing and etc. The retrieval docking component 200 is configured to be captured by and connected to a delivery device 300. The delivery device 300 includes a snare 310 and a sheath 320.

The snare 310 is movably disposed along an axis of the sheath 320 and to loop around the exterior of the leadless pacemaker. With combined reference to FIGS. 1 and 2, during the capture and connection of the leadless pacemaker by and with the delivery device 300, the snare 310 is retracted towards the proximal end, allowing the snare 310 to come into engagement with the retrieval docking component 200, and eventually completing the connection of the retrieval docking component 200 and the delivery device 300.

Referring to FIGS. 4 and 5, in conjunction with FIGS. 1 to 3, in an exemplary embodiment, the retrieval docking component 200 includes a base 210 and a limiting part 220. A distal end of the base 210 along the axial direction (the upper end in FIG. 5) is configured for connection with the leadless pacemaker body 100, and a proximal end of the base 210 along the axial direction (the lower end in FIG. 5) is connected to the limiting part 220. A radial outer dimension of the limiting part 220 is greater than a radial outer dimension of the proximal end of the base 210. The limiting part 220 comprises at least two accommodation grooves 230 along its circumference. The accommodation grooves 230 are open outwardly along radial directions of the base 210 and configured to capture the snare 310 of the delivery device 300. Optionally, the radial outer dimension of the base 210 gradually decreases from its distal end to proximal end. This allows the snare 310, when moving and retracted towards proximal end after capturing the leadless pacemaker body 100, to slide inwardly along the base 210 that gradually decreases towards proximal end.

A description is set forth below of radial outer dimensions of the components described herein. Taking the base 210 as an example, the radial outer dimension of the base 210 refers to the diameter of a maximum outer enveloping circle of its cross-sectional shape that is perpendicular to its axis. In an alternative example, the cross-section of the base 210 is circular, and the radial outer dimension is its outer diameter. In an alternative example, the cross-section of the base 210 is polygonal, and the radial outer dimension is the diameter of its circumcircle. In further alternative embodiments, the cross-section of the base 210 comprises multi-lobed shape, gear shape or otherwise irregular shape, and the radial outer dimension is the diameter of its outer enveloping circle. The radial outer dimensions of the other components are defined in a similar way, and reference can be made to the foregoing description of the radial outer dimension of the base 210 for more details.

It is noted that, by the phrase "the radial outer dimension of the base 210 gradually decreases from its distal end to proximal end", it is intended to mean that the base 210 is overall tapered from the distal end to proximal end, but not that the radial outer dimension of the base 210 necessarily decreases linearly. In some alternative embodiments, the base 210 may include some constant diameter sections where the radial outer dimension of the base 210 remains the same. However, overall, the radial outer dimension of the base 210 generally decreases from the distal end to proximal end.

Optionally, the accommodation grooves 230 extend along axial direction of the base 210 and extend through the limiting part 220. Through configuring the accommodation grooves 230 to extend along axial direction of the base 210, the snare 310, when captured, can extend towards the proximal end along the axial direction of the base 210. This can facilitate the application of a force to the snare 310. It is noted that, by the phrase "the accommodation grooves 230 extend along axial direction of the base 210", it does not strictly mean that the accommodation grooves 230 necessarily extend in parallel to the axis of the base 210. Rather, there may be a small angle between the two. For example, in some embodiment, the angle is configured to be not greater than 30°.

Since the radial outer dimension of the limiting part 220 is greater than the radial outer dimension of the proximal end of the base 210, when the snare 310 of the delivery device 300 moves and is retracted to proximal end after engaging the leadless pacemaker, it will slide to proximal end until it comes into abutment with the limiting part 220. Then, it is stopped by the limiting part 220 that has a larger radial outer dimension and is captured in the accommodation grooves 230, thereby, allowing a reliable and convenient connection to be established between the delivery device 300 and the retrieval docking component 200, increasing success rate of docking and retrieval between the retrieval docking component 200 and the delivery device 300 and reducing docking difficulty. Furthermore, when captured in the accommodation grooves 230, the snare 310 will be prevented from circumferential displacement by the accommodation grooves 230. This can facilitate torque transmission and mutual aligning and docking between the delivery device 300 and the retrieval docking component 200, and hence convenient retrieval of the leadless pacemaker by using the delivery device 300.

Referring to FIG. 6, in an optional example, the snare 310 includes a U-shaped section 311 located at the distal end thereof and extensions 312 joined to the U-shaped section 311 at open ends thereof. When the snare 310 is in an initial configuration where it is not stressed, an angle is formed between the extending direction of the U-shaped section 311 and the extending direction of the extensions 312. Optionally, a circumferential wall of the base 210 forms an angle of 40° to 60° with the axis of the base 210. This can facilitate sliding of the snare 310 towards the proximal end of the base 210, and can help the snare 310 form the angled configuration shown in FIG. 6, which allows two arms of the U-shaped section 311 of the snare 310 to be captured in opposite accommodation grooves 230.

Referring to FIGS. 4 and 5, the accommodation groove 230 comprises an imaginary centerline plane 231 and two groove wall surfaces 232 along the extending direction thereof (the vertical direction in FIG. 5). The two groove wall surfaces 232 are located on opposite sides of the imaginary centerline plane 231. It should be understood that, here, the imaginary centerline plane 231 is taken as an imaginary reference plane for illustrative purposes. The two groove wall surfaces 232 may be of the same shape and symmetrical with respect to the imaginary centerline plane 231. The two groove wall surfaces 232 may be of different shapes and located on opposite sides of the imaginary centerline plane 231.

Among at least one of the accommodation grooves 230, at least one of the groove wall surfaces 232 includes a first guide surface 2321, which is gradually away from the imaginary centerline plane 231 along a direction towards exterior of the limiting part 220 (i.e., away from the center direction of the limiting part 220), thereby forming a flared opening 233. After the snare 310 slides inwardly along the base 210 until it comes into abutment with the limiting part 220, it is additionally retracted towards proximal end, and the sheath 320 is displaced from a location away from an axis of the leadless pacemaker, as shown in FIG. 1, to a location, as shown in FIG. 2, that is, the sheath 320 moves in the direction of the axis of the leadless pacemaker. At the latter location, the snare 310 is in contact with the outer periphery of a proximal end of the limiting part 220 and is captured between the groove wall surfaces 232 of the accommodation grooves 230. By configuring the first guide surface(s) 2321, the accommodation grooves 230 forms outwardly flared opening(s) 233, facilitating sliding of the snare 310 into the accommodation grooves 230. Optionally, the first guide surface 2321 is inclined at an angle of 60° to 80° with respect to the imaginary centerline plane 231, which can facilitate sliding of the snare 310 into the accommodation grooves 230. In some embodiments, the first guide surface 2321 is gradually away from the imaginary centerline plane 231 along a direction towards the distal end of the base 210. That is to say, the first guide surface 2321 flares outwardly and to a distal end as well, in order to facilitate sliding of the snare 310 into the accommodation grooves 230.

It is noted that the groove wall surface 232 includes the first guide surface 2321. The first guide surface 2321 may be provided by a portion of the groove wall surface 232, or the entire groove wall surface 232 may be provided by the first guide surface 2321. In one of the accommodation grooves 230, only one of the groove wall surfaces 232 may include a first guide surface 2321, while the other groove wall surface 232 is an ordinary wall surface extending in the same direction as the accommodation groove 230. Optionally, the two groove wall surfaces 232 of one of the accommodation groove 230 both include a first guide surface 2321. Additionally, among at least two accommodation grooves 230 in the limiting part 220, only one accommodation groove 230 may include the first guide surface(s) 2321, while the remaining one(s) is (are) regular groove(s) extending in the same direction(s) as the accommodation groove(s) 230. Optionally, the two groove wall surfaces 232 of each accommodation groove 230 both include a first guide surface 2321.

With continued reference to FIGS. 4 and 5, in some embodiments, the limiting part 220 includes a second guide surface 221, which is joined to at least one of the groove wall surfaces 232 and is gradually away from the imaginary centerline plane 231 along a direction towards the distal end (the upper end in FIG. 5). It is noted that there is no limitation on the number of the second guiding surfaces 221 here. Among the groove wall surfaces 232 of several accommodation grooves 230, optionally, only one groove wall surface 232 is joined to the second guide surface 221, or all the groove wall surfaces 232 are joined to the second guide surface 221. With combined reference to FIG. 2, after the snare 310 is captured in the accommodation grooves 230, it can be retracted to the proximal end so that the sheath 320 abuts and engages the limiting part 220. The distal U-shaped section of the snare 310 extends substantially circumferentially around the base 210, and the proximal ends of the snare 310 are deflected by the accommodation grooves 230 and then extend to the proximal end substantially along the axial direction of the base 210. The snare 310 forms an approximately 90° angle between its two sections, easily causing the snare 310 to produce concentrated stress at the deflection points, which causes rupture or other undesirable issues. The configuration of the second guide surface 221 allows for a transition of the snare 310 at the deflection points and mitigates the stress concentration on snare 310 to a certain extent. Optionally, the second guide surface 221 is inclined at an angle of 40° to 60° with respect to the imaginary centerline plane 231, which can help snare 310 to form a desired final shape and experience less stress concentration.

Optionally, the accommodation groove 230 has a groove bottom surface 234 along the same direction as the accommodation groove 230, and the groove bottom surface 234 intersects the imaginary centerline plane 231. Among at least one of the accommodation grooves 230, the groove bottom surface 234 includes a third guide surface 2341, which extends to the proximal end (bottom end in FIG. 5) and gradually approaches the axis of the base 210 as it extends. Referring to FIG. 2, in some embodiments, the sheath 320 will come into abutment with the limiting part 220 under an action of the snare 310 being retracted, the proximal end of the snare 310 is inserted into the sheath 320 and its extending direction is coincident with the axis of the base 210, while the groove bottom surfaces 234 of the accommodation grooves 230 are offset from the axis of the base 210, thus, the snare 310 is deflected along the extending direction as it is being pulled out of a proximal end of an accommodation groove 230. With the configuration of the third guide surface 2341, allowing for a transition of the snare 310 at the deflection point at the proximal end of the accommodation groove 230 and thereby mitigate stress concentration on the snare 310 to a certain extent.

Optionally, the limiting part 220 comprises a stop surface 222 oriented towards the distal end, which forms an angle, which is not greater than 90°, with a direction along the axial direction of the base 210 and pointing to distal end (upper end direction in FIG. 5). As a result, an outer edge of the stop surface 222 is closer to the distal end than its inner edge (the two edges would be aligned if the angle were) 90°. The snare 310 gradually slides along the base 210 to the proximal end, and eventually come into abutment with the stop surface 222 and be stopped by the snare 310, rather than sliding beyond the stop surface 222. In the example of FIG. 5, the angle formed by the stop surface 222 and the direction along the axial direction of the base 210 and pointing to distal end is 90°.

Optionally, at least one of the following connections employ a circularly or otherwise a curved transition connection: the joint between the first guide surface(s) 2321 and the remaining portion of the groove wall surface(s) 232, the joint between the second guide surface 221 and the groove wall surface(s) 232, the joint between the second guide surface 221 and the stop surface 222, and the joint between the third guide surface(s) 2341 and the remaining portion of the groove bottom surface(s) 234, in order to reduce resistance to sliding of the snare 310, or stress concentration of the snare 310 when it is tightened.

Referring to FIGS. 1 and 4, a distal end of the sheath 320 is configured to be aligned with the proximal end of the limiting part 220, and abut and engage the proximal end of the limiting part 220 under an action of the snare 310 being retracted towards the proximal end. The limiting part 220 comprises a docking structure 223 oriented towards the proximal end. The docking structure 223 comprises a center coincident with the axis of the base 210 and is configured to mate with the sheath 320. For example, the docking structure 223 may be a cylindrical projection or conical projection formed at the proximal end of the limiting part 220. The distal end of the sheath 320 comprises a mating socket. After the docking structure 223 snaps into the socket of the sheath 320, it allows the sheath 320 to be kept coaxial with the limiting part 220. In addition, after the docking structure 223 snaps into the socket of the sheath 320, it allows the sheath 320 to be prevented from radial displacement with respect to the limiting part 220. This can avoid radial dislodgement of the sheath 320 from the limiting part 220 as a consequence of a radial reaction force generated when the snare 310 is retracted.

Optionally, when the snare 310 is in the initial configuration where it is not stress, the angle between the extending direction of the U-shaped section 311 and the extending direction of the extensions 312 is close or equal to the angle between the second guide surface 221 and the imaginary centerline plane 231. This enables the snare 310 in the rest configuration to comprise a shape that is similar to a shape that the stop surface 222, the second guide surface 221 and the groove wall surfaces 232 together form, which can reduce deformation of the snare 310 to a certain extent and can help reduce its stress concentration.

Referring to FIGS. 4, 7 and 8, optionally, the at least two accommodation grooves 230 are arranged circumferentially around the limiting part 220 at 180° interval. With this arrangement, when the snare 310 slides into two accommodation grooves 230 arranged at 180° interval, an axis of the sheath 320 will coincide with the axis of the base 210 in the retrieval docking component 200. This allows the sheath 320 to align, dock and connect with the limiting part 220.

Optionally, the limiting part 220 comprises four accommodation grooves 230 evenly distributed along its circumference. In the example of FIG. 4, the limiting part 220 comprises four accommodation grooves 230 evenly distributed along its circumference at an angular interval of 90°. With this arrangement, when the snare 310 loops around the leadless pacemaker body 100 and is retracted to the proximal end, it can easily slide into an opposite accommodation grooves 230 (the two accommodation grooves 230 arranged at 60° interval), resulting in a high success rate of retrieval and docking. FIGS. 7 and 8 show two comparative examples. The example of FIG. 7 includes only two accommodation grooves 230 arranged in opposition and is therefore more demanding on an angular position of the limiting part 220 with respect to the snare 310. Obviously, a success rate of retrieval and docking of this example is lower than that of the example of FIG. 4. The comparative example of FIG. 7 includes six accommodation grooves 230 evenly distributed along its circumference. Despite the easy capture of the snare 310 into accommodation grooves 230, it cannot be ensured that the snare 310 is captured in two accommodation grooves 230 arranged at 180° interval. For example, the snare 310 may be captured into adjacent accommodation grooves 230 (the two accommodation grooves 230 arranged at 60° interval), or into two of the accommodation grooves 230 with another accommodation groove 230 intervening between them (the two accommodation grooves 230 arranged at 120° interval). In these cases, the sheath 320 cannot be aligned and docked with respect to the limiting part 220.

Referring to FIGS. 3 and 5, the delivery device 300 further includes a retrieval cup 330 (for the purposes of illustration, only half circumference of the retrieval cup 330 is shown in FIG. 3, but it would be appreciated that the retrieval cup 330 is actually circumferentially continuous). The retrieval cup 330 is movably disposed along the axis of the sheath 320. The retrieval cup 330 has an open distal end and is configured to sheathe the retrieval docking component 200 and the leadless pacemaker body 100 from the proximal end to distal end of the retrieval docking component 200 (from the right end to left end in FIG. 3). In order to mate therewith, the radial outer dimension of the limiting part 220 gradually decreases from distal end to proximal end (from top to bottom in FIG. 5), facilitating the insertion of the retrieval cup 330. A circumferential wall of the limiting part 220 optionally forms an angle of 40° to 60° with the axis of the base 210, which facilitates the insertion of the retrieval cup 330.

In embodiments of the present application, there is also provided a retrieval docking system for a leadless pacemaker, which includes a delivery device 300 and the leadless pacemaker as defined above.

Referring to FIGS. 9 to 14, in one embodiment, the retrieval docking component 200 further includes: capture wings 240. One end of the capture wing 240 is connected to the limiting part 220 (for illustrative purposes, this end is referred to hereinafter as the "connected end 241"), and the other end is a free end 242. When not stressed, the capture wings 240 are in an uncollapsed configuration (as shown in FIGS. 10, 12 and 13) where they extend towards the distal end of the base 210 (upper end in FIG. 12) and gradually extend outwardly, which forms a stretch-out configuration towards distal end. Moreover, the distance from the free ends 242 to the axis of the base 210 is greater than the greatest distance from the outer periphery of the limiting part 220 to the axis of the base 210. With this arrangement, one the one hand, the capture wings 240 can increase the capture area for the snare 310, increasing the success rate of the snare 310 being captured in the accommodation grooves 230. On the other hand, an accommodating space is increased around the joint of the limiting part 220 and the base 210, facilitating the U-shaped section 311 of the snare 310 to be received at the accommodating space around the joint of the limiting part 220 and the base 210 during retrieval and docking. This allows shape and position of the snare 310 to be more easily adjusted, facilitating the successful sliding of the snare 310 into the accommodation grooves 230.

Optionally, under the action of an external confining structure (e.g., the retrieval cup 330), the capture wings 240 can transition into a collapsed configuration (as shown in FIGS. 11 and 14). When the capture wings 240 is in the collapsed configuration, the free ends 242 extends towards distal end (upper end in FIG. 14); a distance from the free ends 242 to the axis of the base 210 is not greater than the greatest distance between the outer periphery of the limiting part 220 and the axis of the base 210. The capture wings 240 are able to transition into the collapsed configuration under an action the retrieval cup 330 being sheathed. On one hand, this will not increase overall radial outer dimension after retrieval, which facilitates passage through blood vessels and tissue around a target. On the other hand, since the free ends 242 of the capture wings 240 in the collapsed configuration are located closer to the center of the limiting part 220 than in the uncollapsed configuration, they can also restrict the position of the snare 310 and avoid the snare 310 from dislodgement, in accordance with some embodiments.

Optionally, the capture wings 240 are elastic sheets and can be transitioned between the uncollapsed and collapsed configurations by elastic deformation. In some exemplary embodiments, the capture wings 240 may be integrally formed with the limiting part 220. In optional embodiments, the capture wings 240 can be independently formed parts relative to the limiting part 220 and attached to the limiting part 220, for example, by welding, adhesive bonding or riveting. Optionally, the capture wings 240 are made of a metal material, such as the superelastic shape-memory alloy TiNi-01, which can ensure that the capture wings 240 can be made with small dimensions while exhibiting suitable stiffness and elasticity. The suitable stiffness allows the capture wings 240 to maintain a certain shape when stopping the snare 310 in the uncollapsed configuration and can prevent them from being too soft to retain the snare 310 when shape and position adjustments are made to the snare 310. The suitable elasticity allows the capture wings 240 to be pushed and transition into the collapsed configuration by the retrieval cup 330 when they abut against each other, ensuring that the capture wings 240 can smoothly rebound and collapse.

Referring to FIGS. 12 to 14, in one exemplary embodiment, the retrieval docking component 200 includes two capture wings 240, and the limiting part 220 comprises two accommodation grooves 230 along its circumference. The capture wings 240 and the accommodation grooves 230 are alternately arranged uniformly along the circumference of the limiting part 220. It is noted that, here, by the phase "the capture wings 240 and the accommodation grooves 230 are alternately arranged uniformly along the circumference of the limiting part 220", it is intended to mean that, along the circumference of the limiting part 220, the two capture wings 240 are spaced apart by one accommodation groove 230, and the two accommodation grooves 230 are spaced apart by one capture wing 240. Each capture wing 240 is spaced by 90° from corresponding adjacent accommodation groove 230, and the two capture wings 240 are arranged at 180° interval. The two accommodation grooves 230 are arranged at 180° interval. With this arrangement, a success rate of initial docking between the snare 310 and the retrieval docking component 200 can be increased.

Of course, the capture wings 240 are not limited to being implemented as sheets, and in some other embodiments, they may be structures of other shapes, such as snap engagement elements, profiled torsion bars, or the like. The retrieval cup 330 includes mating snap engagement elements, limiting grooves or other components for acting on the capture wings 240 to transition it from the uncollapsed configuration to the collapsed configuration. These components can be properly configured according to practical applications, without limiting the scope of the present application in any sense.

On the basis of the retrieval docking component 200 as defined above, in embodiments of the present application, there is also provided a leadless pacemaker including a leadless pacemaker body 100 and the retrieval docking component 200 as defined above. The base 210 of the retrieval docking component 200 is connected to a proximal end of the leadless pacemaker body 100. In embodiments of the present application, there is also provided a leadless pacemaker system including a delivery device 300 and the leadless pacemaker as defined above. Since both the leadless pacemaker and the leadless pacemaker system incorporate the retrieval docking component 200 as defined above, they also offer the same benefits. The structures and principles of other components of the leadless pacemaker and the leadless pacemaker system, please refer to those known in the art, and further description thereof is omitted herein.

In summary, the present application provides a retrieval docking component, a delivery device, a leadless pacemaker and a pacemaker system. The retrieval docking component includes a base and a limiting part. A distal end of the base along the axial direction is configured for connection with a body of an implantable medical device, and a proximal end of the base along the axial direction is connected to the limiting part. A radial outer dimension of the limiting part is greater than a radial outer dimension of the proximal end of the base. The limiting part comprises at least two accommodation grooves along its circumference, which are open outwardly in radial directions of the limiting part and configured for capture a snare of a delivery device. With this arrangement, the structure of the retrieval docking component is simple and provides adequate and reasonable accommodation space to the retrieval snare in a limited space.

After the snare of the delivery device loops the implantable medical device, and moving and retracted towards the proximal end, it can slide along the base to abut and engage with the limiting part, and capture in the accommodation grooves. In this way, enabling the delivery device conveniently and reliably form a connection with the retrieval docking component, increasing success rate of retrieval and docking between the retrieval docking component and the delivery device and reducing the docking difficulty. Further, when the snare is captured in the accommodation grooves, it can also adapt for torque transmission and easy aligning and docking of the delivery device and the retrieval docking component with respect to each other, increasing convenience in retrieval of the implantable medical device.

It is noted that the foregoing several embodiments may be combined. The description presented above is merely that of some optional embodiments of the present application and is not intended to limit the scope thereof in any sense. Any and all changes and modifications made by those of ordinary skill in the art based on the above teachings fall within the scope as defined in the appended claims.

What is claimed is:

1. A retrieval docking component for an implantable medical device, comprising a base and a limiting part,
   wherein a distal end of the base along an axial direction is configured to be connected to a body of the implantable medical device, wherein a proximal end of the base along the axial direction is connected to the limiting part, wherein the limiting part has a radial outer dimension that is greater than a radial outer dimension of the proximal end of the base;
   wherein the limiting part comprises at least two accommodation grooves along a circumference thereof, and wherein each accommodation groove is open outwardly along a radial direction of the base and is configured to capture a snare of a delivery device,
   wherein the retrieval docking component further comprises capture wings, wherein each capture wing comprises a first end that is connected to and at least partially extending through the limiting part and a second end that is a free end, and
   wherein each capture wing comprises, when not stressed, an uncollapsed configuration in which each capture wing is gradually outwardly as extending towards the distal end of the base, wherein a distance from the free end to an axis of the base is greater than a maximum distance between an outer periphery of the limiting part and the axis of the base.

2. The retrieval docking component according to claim 1, wherein a radial outer dimension of the base gradually decreases from the distal end to the proximal end.

3. The retrieval docking component according to claim 1, wherein each accommodation groove extends along an axis of the base and extends through the limiting part.

4. The retrieval docking component according to claim 3, wherein each accommodation groove comprises, along an extending direction thereof, an imaginary centerline plane and two groove wall surfaces that are located on opposite sides of the imaginary centerline plane; and
   wherein at least one groove wall surface of at least one accommodation groove comprises a first guide surface, wherein the first guide surface is gradually away from the imaginary centerline plane along a direction towards an exterior of the limiting part, thereby forming a flared opening.

5. The retrieval docking component according to claim 3, wherein each accommodation groove comprises, along an extending direction thereof, an imaginary centerline plane and two groove wall surfaces that are located on opposite sides of the imaginary centerline plane, wherein the limiting part comprises a second guide surface, and wherein the second guide surface is joined to at least one groove wall surface and is gradually away from the imaginary centerline plane along a direction towards the distal end.

6. The retrieval docking component according to claim 3, wherein each accommodation groove comprises, along an extending direction thereof, an imaginary centerline plane and a groove bottom surface intersecting the imaginary centerline plan; and wherein the groove bottom surface of at least one accommodation groove comprises a third guide surface, and wherein the third guide surface extends to the proximal end and gradually approaches the axis of the base as extending.

7. The retrieval docking component according to claim 1, wherein the radial outer dimension of the limiting part gradually decreases from the distal end to the proximal end.

8. The retrieval docking component according to claim 1, wherein the limiting part comprises a stop surface that is oriented towards the distal end, wherein the stop surface forms an angle not greater than 90° with a direction pointing to the distal end along an axis of the base.

9. The retrieval docking component according to claim 1, wherein the limiting part comprises a docking structure oriented towards the proximal end, wherein the docking structure comprises a center coincident with an axis of the base and is configured to mate with a sheath of the delivery device.

10. The retrieval docking component according to claim 1, wherein the limiting part comprises four accommodation grooves uniformly distributed along a circumference thereof.

11. The retrieval docking component according to claim 1, wherein each capture wing is transitioned under an action of an external confining structure into a collapsed configuration, wherein when each capture wing is in the collapsed configuration, the free end extends towards the distal end, and wherein a distance from the free end to the axis of the base is not greater than the maximum distance between the outer periphery of the limiting part and the axis of the base.

12. The retrieval docking component according to claim 11, wherein each capture wing is an elastic sheet and achieves a transition between the uncollapsed and collapsed configurations by an elastic deformation.

13. The retrieval docking component according to claim 1, wherein the retrieval docking component comprises two capture wings, wherein the limiting part comprises two accommodation grooves along the circumference thereof, and wherein the two capture wings and the two accommodation grooves are alternately arranged uniformly along the circumference of the limiting part.

14. A leadless pacemaker, comprising a leadless pacemaker body and the retrieval docking component according to claim 1, wherein the base of the retrieval docking component is connected to a proximal end of the leadless pacemaker body.

15. A delivery device configured to be connected to a retrieval docking component, wherein the retrieval docking component comprises a base and a limiting part, wherein a distal end of the base along an axial direction is configured to be connected to a body of the implantable medical device, wherein a proximal end of the base along the axial direction is connected to the limiting part, wherein the limiting part has a radial outer dimension that is greater than a radial outer dimension of the proximal end of the base; and wherein the limiting part comprises at least two accommodation grooves along a circumference thereof, and wherein each accommodation groove is open outwardly along a radial direction of the base and is configured to capture a snare of a delivery device, wherein the delivery device comprises a snare and a sheath, wherein the snare is movably disposed along an axis of the sheath, wherein the snare is configured to loop around an exterior of an implantable medical device, wherein during the snare gradually moves towards the proximal end with respect to the sheath, the snare moves to the base of the retrieval docking component, then slides along the retrieval docking component until coming into abutment against the limiting part, and is captured in two of the at least two accommodation grooves;

wherein the sheath comprises a distal end configured to be aligned with a proximal end of the limiting part, and to abut and engage the proximal end of the limiting part under an action of the snare being retracted to the proximal end;

wherein the retrieval docking component further comprises capture wings, wherein each capture wing comprises a first end that is connected to the limiting part and a second end that is a free end, and wherein each capture wing comprises, when not stressed, an uncollapsed configuration in which each capture wing is gradually outwardly as extending towards the distal end of the base, wherein a distance from the free end to an axis of the base is greater than a maximum distance between an outer periphery of the limiting part and the axis of the base.

16. The delivery device according to claim 15, wherein the snare comprises a U-shaped section located at the distal end and extensions joined to the U-shaped section at open ends thereof, wherein when the snare is in an initial configuration where not being stressed, an extending direction of the U-shaped section forms an angle with an extending direction of the extension.

17. The delivery device according to claim 15, further comprising a retrieval cup, wherein the retrieval cup is movably disposed along an axis of the sheath, wherein the retrieval cup comprises a distal end that is open, wherein the retrieval cup is configured to sheathe the retrieval docking component and a body of the implantable medical device from a proximal end to a distal end of the retrieval docking component.

18. The delivery device according to claim 15, wherein a radial outer dimension of the base gradually decreases from the distal end to the proximal end.

19. The delivery device according to claim 15, wherein each accommodation groove extends along an axis of the base and extends through the limiting part.

* * * * *